(12) United States Patent
Van Slyke et al.

(10) Patent No.: US 8,478,376 B2
(45) Date of Patent: Jul. 2, 2013

(54) SYSTEMS AND METHODS FOR DETERMINING PHYSIOLOGICAL INFORMATION USING SELECTIVE TRANSFORM DATA

(75) Inventors: Braddon M. Van Slyke, Arvada, CO (US); Paul Stanley Addison, Edinburgh (GB); James Nicholas Watson, Dunfermline (GB); Scott McGonigle, Edinburgh (GB)

(73) Assignee: Nellcor Puritan Bennett Ireland, Mervue, Galway (IE)

( * ) Notice: Subject to any disclaimer, the term of this patent is extended or adjusted under 35 U.S.C. 154(b) by 1006 days.

(21) Appl. No.: 12/512,143

(22) Filed: Jul. 30, 2009

(65) Prior Publication Data

US 2011/0026784 A1 Feb. 3, 2011

(51) Int. Cl.
*A61B 5/1455* (2006.01)
(52) U.S. Cl.
USPC .......... 600/336; 600/310; 600/322; 600/323; 600/324
(58) Field of Classification Search
USPC ............... 600/310, 323, 324, 330, 473, 476, 600/481, 484, 509, 336; 356/41
See application file for complete search history.

(56) References Cited

U.S. PATENT DOCUMENTS

| | | | |
|---|---|---|---|
| 4,289,141 A | 9/1981 | Cormier | |
| 4,911,167 A * | 3/1990 | Corenman et al. | 600/324 |
| 5,439,483 A | 8/1995 | Duong-Van | |
| 5,482,036 A | 1/1996 | Diab et al. | |
| 5,490,505 A | 2/1996 | Diab et al. | |
| 5,590,650 A | 1/1997 | Genova | |
| 5,632,272 A | 5/1997 | Diab et al. | |
| 5,685,299 A | 11/1997 | Diab et al. | |
| 5,769,785 A | 6/1998 | Diab et al. | |
| 5,778,881 A | 7/1998 | Sun et al. | |
| 5,795,304 A | 8/1998 | Sun et al. | |
| 5,797,840 A | 8/1998 | Akselrod et al. | |
| 5,827,195 A | 10/1998 | Lander | |
| 5,924,980 A | 7/1999 | Coetzee | |
| 5,967,995 A | 10/1999 | Shusterman et al. | |
| 6,002,952 A | 12/1999 | Diab et al. | |
| 6,036,642 A | 3/2000 | Diab et al. | |
| 6,036,653 A | 3/2000 | Baba et al. | |

(Continued)

FOREIGN PATENT DOCUMENTS

| | | |
|---|---|---|
| JP | 09-084776 | 3/1997 |
| WO | WO 01/25802 | 4/2001 |

(Continued)

OTHER PUBLICATIONS

Addison, Paul S., The Illustrated Wavelet Transform Handbook, Taylor & Francis Group, 2002.

(Continued)

*Primary Examiner* — Eric Winakur
*Assistant Examiner* — Chu Chuan (JJ) Liu

(57) ABSTRACT

According to embodiments, a pulse band region is identified in a wavelet scalogram of a physiological signal (e.g., a plethysmograph or photoplethysmograph signal). Components of the scalogram at scales larger than the identified pulse band region are then used to determine a baseline signal in wavelet space. The baseline signal may then be used to normalize the physiological signal. Physiological information may be determined from the normalized signal. For example, oxygen saturation may be determined using a ratio of ratios or any other suitable technique.

20 Claims, 13 Drawing Sheets

U.S. PATENT DOCUMENTS

| | | | |
|---|---|---|---|
| 6,094,592 | A | 7/2000 | Yorkey et al. |
| 6,095,984 | A | 8/2000 | Amano et al. |
| 6,117,075 | A | 9/2000 | Barnea |
| 6,129,675 | A | 10/2000 | Jay |
| 6,135,952 | A | 10/2000 | Coetzee |
| 6,135,966 | A | 10/2000 | Ko |
| 6,171,257 | B1 | 1/2001 | Weil et al. |
| 6,171,258 | B1 | 1/2001 | Karakasoglu et al. |
| 6,206,830 | B1 | 3/2001 | Diab et al. |
| 6,208,951 | B1 | 3/2001 | Kumar et al. |
| 6,263,222 | B1 | 7/2001 | Diab et al. |
| 6,293,915 | B1 | 9/2001 | Amano et al. |
| 6,325,761 | B1 | 12/2001 | Jay |
| 6,361,501 | B1 | 3/2002 | Amano et al. |
| 6,393,311 | B1 | 5/2002 | Edgar, Jr. et al. |
| 6,501,975 | B2 | 12/2002 | Diab et al. |
| 6,561,986 | B2 | 5/2003 | Baura et al. |
| 6,608,934 | B2 | 8/2003 | Scheirer et al. |
| 6,654,623 | B1 | 11/2003 | Kästle |
| RE38,492 | E | 4/2004 | Diab et al. |
| 6,810,277 | B2 | 10/2004 | Edgar, Jr. et al. |
| 6,931,269 | B2 | 8/2005 | Terry |
| 7,001,337 | B2 | 2/2006 | Dekker |
| 7,020,507 | B2 | 3/2006 | Scharf et al. |
| 7,035,679 | B2 | 4/2006 | Addison et al. |
| 7,043,293 | B1 | 5/2006 | Baura |
| 7,054,453 | B2 | 5/2006 | Causevic et al. |
| 7,054,454 | B2 | 5/2006 | Causevic et al. |
| 7,079,888 | B2 | 7/2006 | Oung et al. |
| 7,167,746 | B2 | 1/2007 | Pederson |
| 7,171,269 | B1 | 1/2007 | Addison et al. |
| 7,173,525 | B2 | 2/2007 | Albert |
| 7,203,267 | B2 | 4/2007 | De Man et al. |
| 7,225,013 | B2 | 5/2007 | Geva et al. |
| 7,254,500 | B2 | 8/2007 | Makeig et al. |
| 7,289,835 | B2 | 10/2007 | Mansfield et al. |
| 7,515,949 | B2 | 4/2009 | Norris |
| 7,519,488 | B2 | 4/2009 | Fu et al. |
| 7,523,011 | B2 | 4/2009 | Akiyama et al. |
| 7,738,936 | B1 * | 6/2010 | Turcott .................. 600/339 |
| 2003/0163057 | A1 | 8/2003 | Flick et al. |
| 2005/0043616 | A1 | 2/2005 | Chinchoy |
| 2005/0043763 | A1 | 2/2005 | Marcovecchio et al. |
| 2006/0209631 | A1 | 9/2006 | Melese et al. |
| 2006/0229519 | A1 | 10/2006 | Fujiwara et al. |
| 2006/0258921 | A1 | 11/2006 | Addison et al. |
| 2006/0265022 | A1 | 11/2006 | John et al. |
| 2007/0021673 | A1 | 1/2007 | Arbel et al. |
| 2007/0073120 | A1 | 3/2007 | Li et al. |
| 2007/0073124 | A1 | 3/2007 | Li et al. |
| 2007/0167694 | A1 | 7/2007 | Causevic et al. |
| 2007/0167851 | A1 | 7/2007 | Vitali et al. |
| 2007/0282212 | A1 | 12/2007 | Sierra et al. |
| 2008/0045832 | A1 | 2/2008 | McGrath |
| 2008/0082018 | A1 | 4/2008 | Sackner et al. |
| 2008/0214903 | A1 | 9/2008 | Orbach |
| 2008/0243021 | A1 | 10/2008 | Causevic et al. |

FOREIGN PATENT DOCUMENTS

| | | |
|---|---|---|
| WO | WO 01/62152 | 8/2001 |
| WO | WO 01/082099 | 11/2001 |
| WO | WO 03/000125 | 1/2003 |
| WO | WO 03/055395 | 7/2003 |
| WO | WO 2004/105601 | 12/2004 |
| WO | WO 2005/096170 | 10/2005 |
| WO | WO 2006/085120 | 8/2006 |

OTHER PUBLICATIONS

Addison, Paul, "The Little Wave with the Big Future," Physics World, Mar. 2004, pp. 35-39.

Clifton, David, Douglas, J. Graham, Addison, Paul S., Watson, James N., "Measurement of Respiratory Rate from the Photoplethysmogram in Chest Clinic Patients," Journal of Clinical Monitoring and Computing, 2006.

Legarreta, I. Romero, Addison, P. S., Reed, M. J., Grubb, N. Clegg, G. R., Robertson, C. E., Watson, J. N., "Continuous Wavelet Transform Modulus Maxima Analysis of the Electrocardiogram: Beat Characterisation and Beat-to-Beat Measurement," International Journal of Wavelets, Multiresolution and Information Processing, vol. 3, No. 1, 2004, pp. 1-24.

Leonard, Paul A., Douglas, J. Graham, Grubb, Neil R., Clifton, David, Addison, Paul S., Watson, James N., "A Fully Automated Algorithm for the Determination of Respiratory Rate From the Photoplethysmogram," Journal of Clinical Monitoring and Computing, 2006.

Leonard, Paul a., Clifton, David, Addison, Paul S., Watson, James N., Beattie, Tom "An Automated Algorithm for Determining Respiratory Rate by Photoplethysmogram in Children," Acta Paediatricia, 2006; 95: 1124-1128.

Yamada, Michio, "Wavelet Analysis and Its Application," Journal of the Institute of Electronics, Information and Communication Engineers, vol. 76, No. 5, May 1993, pp. 518-528.

* cited by examiner

SYSTEMS AND METHODS FOR DETERMINING PHYSIOLOGICAL INFORMATION USING SELECTIVE TRANSFORM DATA

SUMMARY

The present disclosure relates to signal processing and, more particularly, the present disclosure relates to processing, for example, a photoplethysmograph (PPG) signal to determine information about physiological states and/or processes of a patient.

As described in more detail below, a pulse oximeter may be used to determine oxygen saturation, pulse rate, and other physiological parameters by an analysis of an optically sensed plethysmograph. The oximeter may pass light using a light source through blood perfused tissue and photoelectrically sense the absorption of light in the tissue.

Various signals processing techniques may be employed in connection with a detected PPG signal in order to more easily determine physiological information of a patient. For example, a continuous wavelet transform of a PPG signal may be particularly good at partitioning signal components for extraction and interrogation. The extracted signal components may then be analyzed and used to determine various physiological information of a patient. As described in U.S. patent application Ser. No. 12/245,400, filed Oct. 3, 2008, and Ser. No. 12/244,141, filed Oct. 2, 2008, which are both hereby incorporated by reference herein in their entireties, sometimes these extracted signal components may be normalized using a signal baseline, or baseline changes in the PPG signal (or some transform of the PPG signal) may be used to detect events (e.g., cardiac or arousal events).

In an embodiment, a signal processing system may identify a pulse band in a scalogram of the continuous wavelet transform of a physiological signal (e.g., a PPG signal). The extent of the pulse band across scales may then be defined. In an embodiment, signal components at scales larger than the defined pulse band region may be considered as part of the baseline signal, B. The PPG signal (or some transform of the PPG signal) may then be normalized using the baseline signal and used to determine at least one physiological parameter. For example, oxygen saturation may be determined by computing a ratio of ratios, as described in more detail below, using the normalized signal. In order to determine the baseline signal B, the signal processing system may operate directly on a received physiological signal itself (e.g., a PPG signal), some transform of a received physiological signal (e.g., a continuous wavelet transform of the signal), a scalogram derived from the transformed signal, a wavelet ratio surface, the real part of the wavelet transform, the imaginary part of the wavelet transform, the modulus of the wavelet transform, the energy density of the wavelet transform, or any combination of the foregoing signals.

In an embodiment, the signal processing system may first identify a pulse band ridge in a scalogram of the continuous wavelet transform of a physiological signal (e.g., a PPG signal). The ridge may be defined, in some embodiments, as the maxima with respect to time of the band formed by the pulse components of the signal. In some embodiments, the pulse band ridge may be identified directly from the wavelet transform scalogram. In some embodiments, the pulse band ridge may be identified, at least in part, from externally supplied data (e.g., a heart rate supplied by a physiological monitoring system or other device). In some embodiments, the pulse band ridge may be identified, at least in part, from both the wavelet transform scalogram itself and externally supplied data.

In an embodiment, after the pulse band ridge is identified, the pulse band region may then be defined. The pulse band region may be selected to include, for example, the region of influence of the pulse components on the transform surface. In some embodiments, this region may extend on one or both sides of the pulse band ridge until a threshold roll off of some measure (e.g., energy density). In some embodiments, the pulse band region may extend on one or both sides of the pulse band ridge until some percentage of ridge peak energy is encountered. For example, the regions may extend on one or both sides of the pulse band ridge until a 0.5% ridge peak energy is encountered. The pulse band region may additionally or alternatively be defined as a distance from the pulse band ridge on one or both sides of the ridge. In yet another embodiment, the pulse band regions may be defined using a threshold that sets a minima boundary between the pulse band and another larger-scale band which minimizes the impact of the larger-scale band.

After the pulse band region is defined, the lower boundary of this region may be used to partition the pulse information in the wavelet scalogram from other larger-scale oscillations in the signal. For example, the region of the wavelet scalogram at scales larger than the defined pulse band region (e.g., regions below the defined pulse band region in the scalogram) may contain the larger scale signal components, but not the DC component. This region may be defined as the larger-scale (LS) signal. The signal baseline, B, may then be computed as the LS signal or the LS signal plus the DC component in some embodiments. The DC component may then be computed separately, added to the LS signal, and used to normalize the PPG signal.

In an embodiment, the LS signal may be computed by taking the inverse continuous wavelet transform of the larger-scale components in the wavelet scalogram (e.g., the components below the pulse band in the scalogram). The LS signal may then be added to a mean signal component or the DC component to form the baseline B.

More than one baseline signal may be computed in some embodiments. For example, a baseline for a red PPG signal and a baseline for an infrared PPG signal may both be computed and used to normalize their respective PPG signals. Physiological parameters may then be determined from one or more of the normalized PPG signals. For example, oxygen saturation may be determined using the ratio of ratios, as described below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above and other features of the present disclosure, its nature and various advantages will be more apparent upon consideration of the following detailed description, taken in conjunction with the accompanying drawings in which.

DETAILED DESCRIPTION

Figure 1:
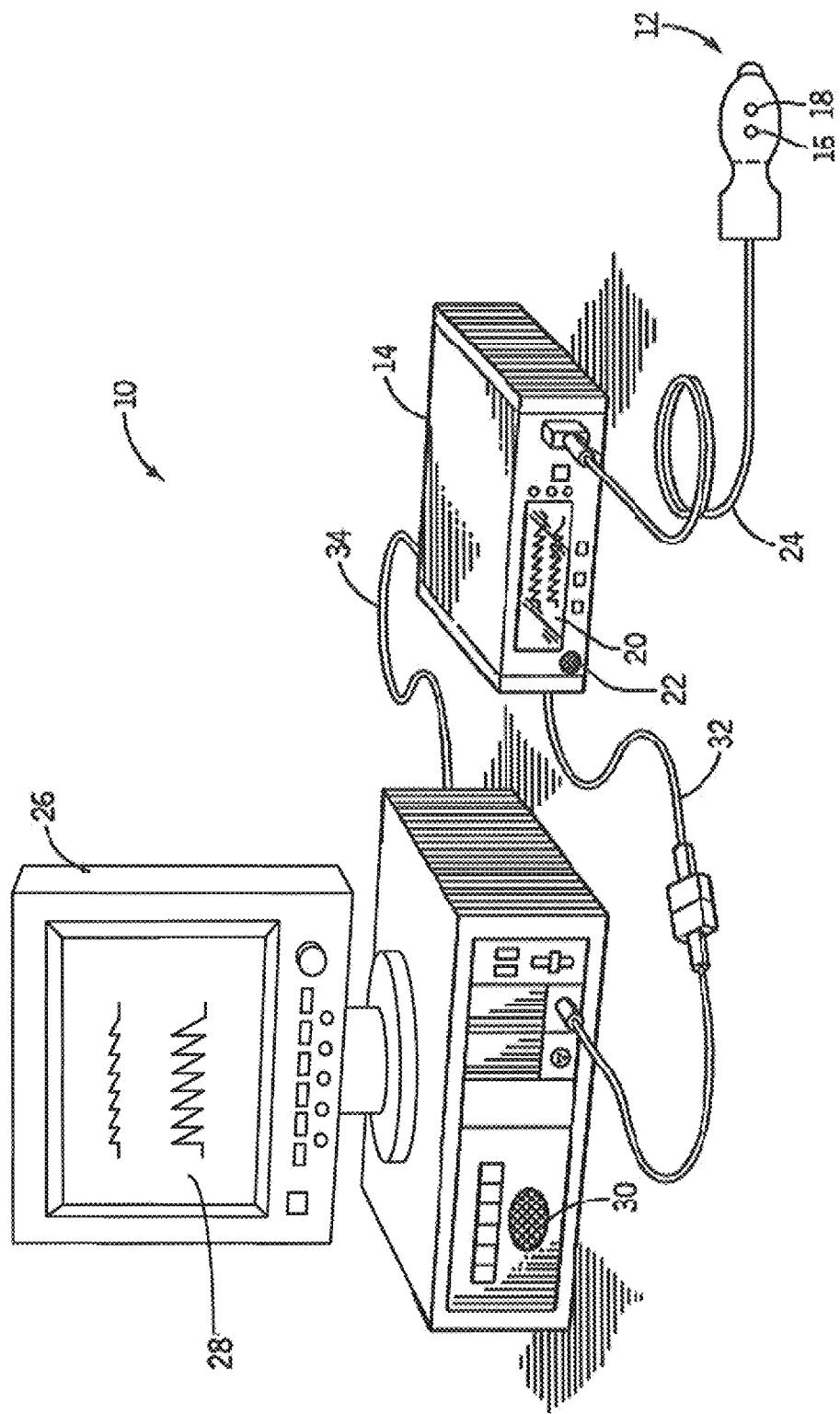
FIG. 1 shows an illustrative pulse oximetry system in accordance with an embodiment.

An oximeter is a medical device that may determine the oxygen saturation of the blood. One common type of oximeter is a pulse oximeter, which may indirectly measure the oxygen saturation of a patient's blood (as opposed to measuring oxygen saturation directly by analyzing a blood sample taken from the patient) and changes in blood volume in the skin. Ancillary to the blood oxygen saturation measurement, pulse oximeters may also be used to measure the pulse rate of the patient. Pulse oximeters typically measure and display various blood flow characteristics including, but not limited to, the oxygen saturation of hemoglobin in arterial blood.

An oximeter may include a light sensor that is placed at a site on a patient, typically a fingertip, toe, forehead or earlobe, or in the case of a neonate, across a foot. The oximeter may pass light using a light source through blood perfused tissue and photoelectrically sense the absorption of light in the tissue. For example, the oximeter may measure the intensity of light that is received at the light sensor as a function of time. A signal representing light intensity versus time or a mathematical manipulation of this signal (e.g., a scaled version thereof, a log taken thereof, a scaled version of a log taken thereof, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate the amount of the blood constituent (e.g., oxyhemoglobin) being measured as well as the pulse rate and when each individual pulse occurs.

The light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption. Red and infrared wavelengths may be used because it has been observed that highly oxygenated blood will absorb relatively less red light and more infrared light than blood with a lower oxygen saturation. By comparing the intensities of two wavelengths at different points in the pulse cycle, it is possible to estimate the blood oxygen saturation of hemoglobin in arterial blood.

When the measured blood parameter is the oxygen saturation of hemoglobin, a convenient starting point assumes a saturation calculation based on Lambert-Beer's law. The following notation will be used herein:

$$I(\lambda,t)=I_o(\lambda)\exp(-(s\beta_o(\lambda)+(1-s)\beta_r(\lambda))l(t)) \quad (1)$$

where:
$\lambda$=wavelength;
t=time;
I=intensity of light detected;
$I_o$=intensity of light transmitted;
s=oxygen saturation;
$\beta_o$, $\beta_r$=empirically derived absorption coefficients; and
l(t)=a combination of concentration and path length from emitter to detector as a function of time.

The traditional approach measures light absorption at two wavelengths (e.g., red and infrared (IR)), and then calculates saturation by solving for the "ratio of ratios" as follows.

1. First, the natural logarithm of (1) is taken ("log" will be used to represent the natural logarithm) for IR and Red $$\log I = \log I_o - (s\beta_o + (1-s)\beta_r)l \quad (2)$$

2. (2) is then differentiated with respect to time $$\frac{d\log I}{dt} = -(s\beta_o + (1-s)\beta_r)\frac{dl}{dt} \quad (3)$$

3. Red (3) is divided by IR (3)

$$\frac{d\log I(\lambda_R)/dt}{d\log I(\lambda_{IR})/dt} = \frac{s\beta_o(\lambda_R) + (1-s)\beta_r(\lambda_R)}{s\beta_o(\lambda_{IR}) + (1-s)\beta_r(\lambda_{IR})} \quad (4)$$

4. Solving for s $$s = \frac{\frac{d\log I(\lambda_{IR})}{dt}\beta_r(\lambda_R) - \frac{d\log I(\lambda_R)}{dt}\beta_r(\lambda_{IR})}{\frac{d\log I(\lambda_R)}{dt}(\beta_o(\lambda_{IR}) - \beta_r(\lambda_{IR})) - \frac{d\log I(\lambda_{IR})}{dt}(\beta_o(\lambda_R) - \beta_r(\lambda_R))}$$

Note in discrete time $$\frac{d\log I(\lambda, t)}{dt} \simeq \log I(\lambda, t_2) - \log I(\lambda, t_1)$$

Using log A-log B=log A/B, $$\frac{d\log I(\lambda, t)}{dt} \simeq \log\left(\frac{I(t_2, \lambda)}{I(t_1, \lambda)}\right)$$

So, (4) can be rewritten as $$\frac{\frac{d\log I(\lambda_R)}{dt}}{\frac{d\log I(\lambda_{IR})}{dt}} \simeq \frac{\log\left(\frac{I(t_1,\lambda_R)}{I(t_2,\lambda_R)}\right)}{\log\left(\frac{I(t_1,\lambda_{IR})}{I(t_2,\lambda_{IR})}\right)} = R \quad (5)$$

where R represents the "ratio of ratios." Solving (4) for s using (5) gives $$s = \frac{\beta_r(\lambda_R) - R\beta_r(\lambda_{IR})}{R(\beta_o(\lambda_{IR}) - \beta_r(\lambda_{IR})) - \beta_o(\lambda_R) + \beta_r(\lambda_R)}.$$

From (5), R can be calculated using two points (e.g., PPG maximum and minimum), or a family of points. One method using a family of points uses a modified version of (5). Using the relationship $$\frac{d\log I}{dt} = \frac{dI/dt}{I} \quad (6)$$

now (5) becomes $$\frac{\frac{d\log I(\lambda_R)}{dt}}{\frac{d\log I(\lambda_{IR})}{dt}} \simeq \frac{\frac{I(t_2,\lambda_R) - I(t_1,\lambda_R)}{I(t_1,\lambda_R)}}{\frac{I(t_2,\lambda_{IR}) - I(t_1,\lambda_{IR})}{I(t_1,\lambda_{IR})}} \quad (7)$$
$$= \frac{[I(t_2,\lambda_R) - I(t_1,\lambda_R)]I(t_1,\lambda_{IR})}{[I(t_2,\lambda_{IR}) - I(t_1,\lambda_{IR})]I(t_1,\lambda_R)}$$
$$= R$$

which defines a cluster of points whose slope of y versus x will give R where $$x(t) = [I(t_2,\lambda_{IR}) - I(t_1,\lambda_{IR})]I(t_1,\lambda_R)$$

$$y(t) = [I(t_2,\lambda_R) - I(t_1,\lambda_R)]I(t_1,\lambda_{IR}) \quad (8)$$

$$y(t) = Rx(t)$$

FIG. 1 is a perspective view of an embodiment of a pulse oximetry system 10. System 10 may include a sensor 12 and a pulse oximetry monitor 14. Sensor 12 may include an emitter 16 for emitting light at two or more wavelengths into a patients tissue. A detector 18 may also be provided in sensor 12 for detecting the light originally from emitter 16 that emanates from the patients tissue after passing through the tissue.

According to another embodiment and as will be described, system 10 may include a plurality of sensors forming a sensor array in lieu of single sensor 12. Each of the sensors of the sensor array may be a complementary metal oxide semiconductor (CMOS) sensor. Alternatively, each sensor of the array may be charged coupled device (CCD) sensor. In another embodiment, the sensor array may be made up of a combination of CMOS and CCD sensors. The CCD sensor may comprise a photoactive region and a transmission region for receiving and transmitting data whereas the CMOS sensor may be made up of an integrated circuit having an array of pixel sensors. Each pixel may have a photodetector and an active amplifier.

According to an embodiment, emitter 16 and detector 18 may be on opposite sides of a digit such as a finger or toe, in which case the light that is emanating from the tissue has passed completely through the digit. In an embodiment, emitter 16 and detector 18 may be arranged so that light from emitter 16 penetrates the tissue and is reflected by the tissue into detector 18, such as a sensor designed to obtain pulse oximetry data from a patient's forehead.

In an embodiment, the sensor or sensor array may be connected to and draw its power from monitor 14 as shown. In another embodiment, the sensor may be wirelessly connected to monitor 14 and include its own battery or similar power supply (not shown). Monitor 14 may be configured to calculate physiological parameters based at least in part on data received from sensor 12 relating to light emission and detection. In an alternative embodiment, the calculations may be performed on the monitoring device itself and the result of the oximetry reading may be passed to monitor 14. Further, monitor 14 may include a display 20 configured to display the physiological parameters or other information about the system. In the embodiment shown, monitor 14 may also include a speaker 22 to provide an audible sound that may be used in various other embodiments, such as for example, sounding an audible alarm in the event that a patient's physiological parameters are not within a predefined normal range.

In an embodiment, sensor 12, or the sensor array, may be communicatively coupled to monitor 14 via a cable 24. However, in other embodiments, a wireless transmission device (not shown) or the like may be used instead of or in addition to cable 24.

In the illustrated embodiment, pulse oximetry system 10 may also include a multi-parameter patient monitor 26. The monitor may be cathode ray tube type, a flat panel display (as shown) such as a liquid crystal display (LCD) or a plasma display, or any other type of monitor now known or later developed. Multi-parameter patient monitor 26 may be configured to calculate physiological parameters and to provide a display 28 for information from monitor 14 and from other medical monitoring devices or systems (not shown). For example, multiparameter patient monitor 26 may be configured to display an estimate of a patient's blood oxygen saturation generated by pulse oximetry monitor 14 (referred to as an "SpO$_2$" measurement), pulse rate information from monitor 14 and blood pressure from a blood pressure monitor (not shown) on display 28.

Monitor 14 may be communicatively coupled to multi-parameter patient monitor 26 via a cable 32 or 34 that is coupled to a sensor input port or a digital communications port, respectively and/or may communicate wirelessly (not shown). In addition, monitor 14 and/or multi-parameter patient monitor 26 may be coupled to a network to enable the sharing of information with servers or other workstations (not shown). Monitor 14 may be powered by a battery (not shown) or by a conventional power source such as a wall outlet.

Figure 2:
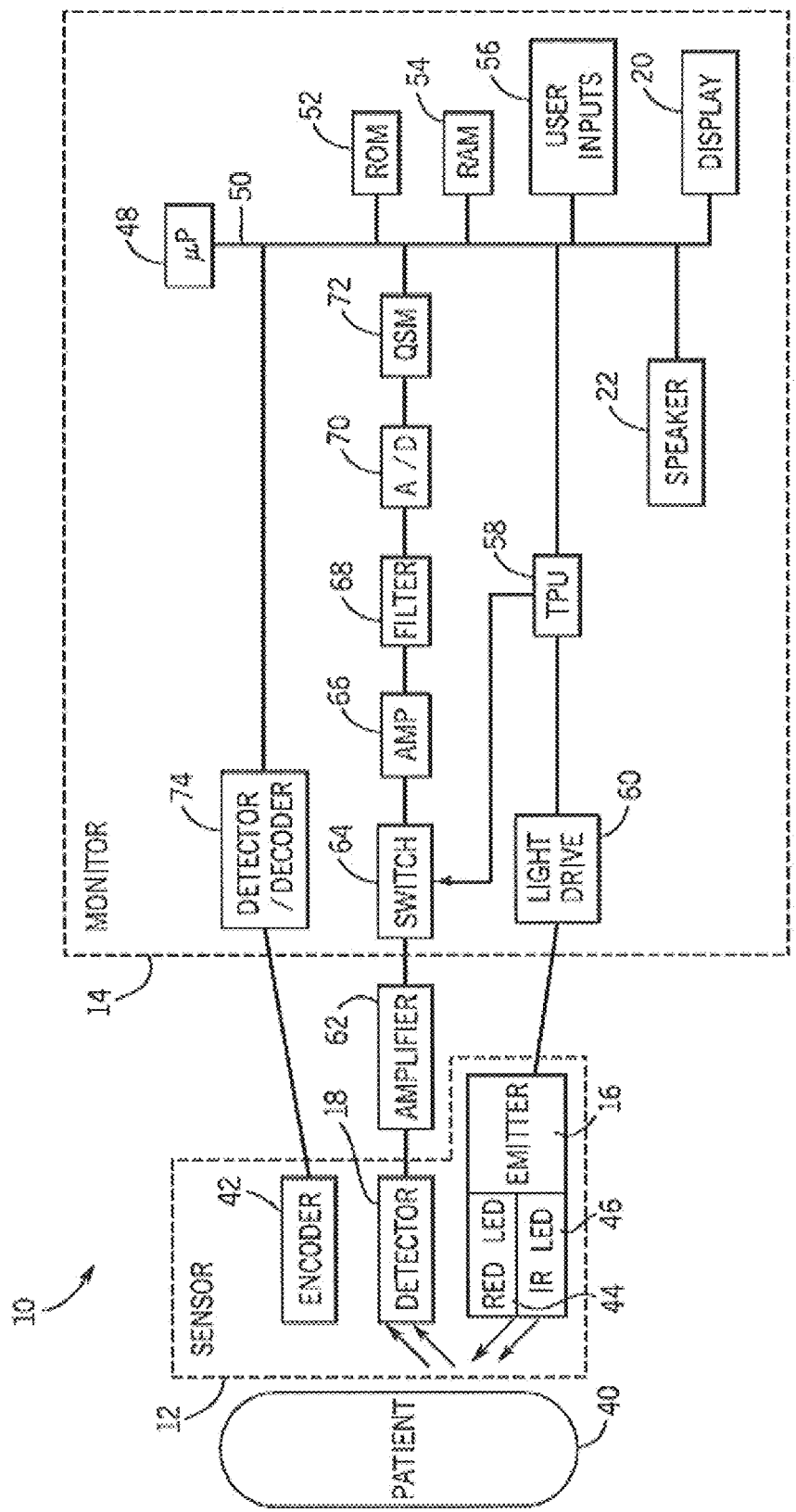
FIG. 2 is a block diagram of the illustrative pulse oximetry system of FIG. 1 coupled to a patient in accordance with an embodiment.

FIG. 2 is a block diagram of a pulse oximetry system, such as pulse oximetry system 10 of FIG. 1, which may be coupled to a patient 40 in accordance with an embodiment. Certain illustrative components of sensor 12 and monitor 14 are illustrated in FIG. 2. Sensor 12 may include emitter 16, detector 18, and encoder 42. In the embodiment shown, emitter 16 may be configured to emit at least two wavelengths of light (e.g., RED and IR) into a patient's tissue 40. Hence, emitter 16 may include a RED light emitting light source such as RED light emitting diode (LED) 44 and an IR light emitting light source such as IR LED 46 for emitting light into the patient's tissue 40 at the wavelengths used to calculate patient's physiological parameters. In one embodiment, the RED wavelength may be between about 600 nm and about 700 nm, and the IR wavelength may be between about 800 nm and about 1000 nm. In embodiments where a sensor array is used in place of single sensor, each sensor may be configured to emit a single wavelength. For example, a first sensor emits only a RED light while a second only emits an IR light.

It will be understood that, as used herein, the term "light" may refer to energy produced by radiative sources and may include one or more of ultrasound, radio, microwave, millimeter wave, infrared, visible, ultraviolet, gamma ray or X-ray electromagnetic radiation. As used herein, light may also include any wavelength within the radio, microwave, infrared, visible, ultraviolet, or X-ray spectra, and that any suitable wavelength of electromagnetic radiation may be appropriate for use with the present techniques. Detector 18 may be chosen to be specifically sensitive to the chosen targeted energy spectrum of the emitter 16.

In an embodiment, detector 18 may be configured to detect the intensity of light at the RED and IR wavelengths. Alternatively, each sensor in the array may be configured to detect an intensity of a single wavelength. In operation, light may enter detector 18 after passing through the patient's tissue 40. Detector 18 may convert the intensity of the received light into an electrical signal. The light intensity is directly related to the absorbance and/or reflectance of light in the tissue 40. That is, when more light at a certain wavelength is absorbed or reflected, less light of that wavelength is received from the tissue by the detector 18. After converting the received light to an electrical signal, detector 18 may send the signal to monitor 14, where physiological parameters may be calculated based on the absorption of the RED and IR wavelengths in the patient's tissue 40.

In an embodiment, encoder 42 may contain information about sensor 12, such as what type of sensor it is (e.g., whether the sensor is intended for placement on a forehead or digit) and the wavelengths of light emitted by emitter 16. This information may be used by monitor 14 to select appropriate algorithms, lookup tables and/or calibration coefficients stored in monitor 14 for calculating the patient's physiological parameters.

Encoder 42 may contain information specific to patient 40, such as, for example, the patients age, weight, and diagnosis. This information may allow monitor 14 to determine, for example, patient-specific threshold ranges in which the patients physiological parameter measurements should fall and to enable or disable additional physiological parameter algorithms. Encoder 42 may, for instance, be a coded resistor which stores values corresponding to the type of sensor 12 or the type of each sensor in the sensor array, the wavelengths of light emitted by emitter 16 on each sensor of the sensor array, and/or the patient's characteristics. In another embodiment, encoder 42 may include a memory on which one or more of the following information may be stored for communication to monitor 14: the type of the sensor 12; the wavelengths of light emitted by emitter 16; the particular wavelength each sensor in the sensor array is monitoring; a signal threshold for each sensor in the sensor array; any other suitable information; or any combination thereof.

In an embodiment, signals from detector 18 and encoder 42 may be transmitted to monitor 14. In the embodiment shown, monitor 14 may include a general-purpose microprocessor 48 connected to an internal bus 50. Microprocessor 48 may be adapted to execute software, which may include an operating system and one or more applications, as part of performing the functions described herein. Also connected to bus 50 may be a read-only memory (ROM) 52, a random access memory (RAM) 54, user inputs 56, display 20, and speaker 22.

RAM 54 and ROM 52 are illustrated by way of example, and not limitation. Any suitable computer-readable media may be used in the system for data storage. Computer-readable media are capable of storing information that can be interpreted by microprocessor 48. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

In the embodiment shown, a time processing unit (TPU) 58 may provide timing control signals to a light drive circuitry 60, which may control when emitter 16 is illuminated and multiplexed timing for the RED LED 44 and the IR LED 46. TPU 58 may also control the gating-in of signals from detector 18 through an amplifier 62 and a switching circuit 64. These signals are sampled at the proper time, depending upon which light source is illuminated. The received signal from detector 18 may be passed through an amplifier 66, a low pass filter 68, and an analog-to-digital converter 70. The digital data may then be stored in a queued serial module (QSM) 72 (or buffer) for later downloading to RAM 54 as QSM 72 fills up. In one embodiment, there may be multiple separate parallel paths having amplifier 66, filter 68, and A/D converter 70 for multiple light wavelengths or spectra received.

In an embodiment, microprocessor 48 may determine the patient's physiological parameters, such as $SpO_2$ and pulse rate, using various algorithms and/or look-up tables based on the value of the received signals and/or data corresponding to the light received by detector 18. Signals corresponding to information about patient 40, and particularly about the intensity of light emanating from a patient's tissue over time, may be transmitted from encoder 42 to a decoder 74. These signals may include, for example, encoded information relating to patient characteristics. Decoder 74 may translate these signals to enable the microprocessor to determine the thresholds based on algorithms or look-up tables stored in ROM 52. User inputs 56 may be used to enter information about the patient, such as age, weight, height, diagnosis, medications, treatments, and so forth. In an embodiment, display 20 may exhibit a list of values which may generally apply to the patient, such as, for example, age ranges or medication families, which the user may select using user inputs 56.

The optical signal through the tissue can be degraded by noise, among other sources. One source of noise is ambient light that reaches the light detector. Another source of noise is electromagnetic coupling from other electronic instruments. Movement of the patient also introduces noise and affects the signal. For example, the contact between the detector and the skin, or the emitter and the skin, can be temporarily disrupted when movement causes either to move away from the skin. In addition, because blood is a fluid, it responds differently than the surrounding tissue to inertial effects, thus resulting in momentary changes in volume at the point to which the oximeter probe is attached.

Noise (e.g., from patient movement) can degrade a pulse oximetry signal relied upon by a physician, without the physicians awareness. This is especially true if the monitoring of the patient is remote, the motion is too small to be observed, or the doctor is watching the instrument or other parts of the patient, and not the sensor site. Processing pulse oximetry (i.e., PPG) signals may involve operations that reduce the amount of noise present in the signals or otherwise identify noise components in order to prevent them from affecting measurements of physiological parameters derived from the PPG signals.

It will be understood that the present disclosure is applicable to any suitable signals and that PPG signals are used merely for illustrative purposes. Those skilled in the art will recognize that the present disclosure has wide applicability to other signals including, but not limited to other biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In one embodiment, a PPG signal may be transformed using a continuous wavelet transform. Information derived from the transform of the PPG signal (i.e., in wavelet space) may be used to provide measurements of one or more physiological parameters.

The continuous wavelet transform of a signal x(t) in accordance with the present disclosure may be defined as $$T(a, b) = \frac{1}{\sqrt{a}} \int_{-\infty}^{+\infty} x(t)\psi^*\left(\frac{t-b}{a}\right) dt \quad (9)$$

where $\psi^*(t)$ is the complex conjugate of the wavelet function $\psi(t)$, a is the dilation parameter of the wavelet and b is the location parameter of the wavelet. The transform given by equation (9) may be used to construct a representation of a signal on a transform surface. The transform may be regarded as a time-scale representation. Wavelets are composed of a range of frequencies, one of which may be denoted as the characteristic frequency of the wavelet, where the characteristic frequency associated with the wavelet is inversely proportional to the scale a. One example of a characteristic frequency is the dominant frequency. Each scale of a particular wavelet may have a different characteristic frequency. The underlying mathematical detail required for the implementation within a time-scale can be found, for example, in Paul S. Addison, The Illustrated Wavelet Transform Handbook (Taylor & Francis Group 2002), which is hereby incorporated by reference herein in its entirety.

The continuous wavelet transform decomposes a signal using wavelets, which are generally highly localized in time. The continuous wavelet transform may provide a higher resolution relative to discrete transforms, thus providing the ability to garner more information from signals than typical frequency transforms such as Fourier transforms (or any other spectral techniques) or discrete wavelet transforms. Continuous wavelet transforms allow for the use of a range of wavelets with scales spanning the scales of interest of a signal such that small scale signal components correlate well with the smaller scale wavelets and thus manifest at high energies at smaller scales in the transform. Likewise, large scale signal components correlate well with the larger scale wavelets and thus manifest at high energies at larger scales in the transform. Thus, components at different scales may be separated and extracted in the wavelet transform domain. Moreover, the use of a continuous range of wavelets in scale and time position allows for a higher resolution transform than is possible relative to discrete techniques.

In addition, transforms and operations that convert a signal or any other type of data into a spectral (i.e., frequency) domain necessarily create a series of frequency transform values in a two-dimensional coordinate system where the two dimensions may be frequency and, for example, amplitude. For example, any type of Fourier transform would generate such a two-dimensional spectrum. In contrast, wavelet transforms, such as continuous wavelet transforms, are required to be defined in a three-dimensional coordinate system and generate a surface with dimensions of time, scale and, for example, amplitude. Hence, operations performed in a spectral domain cannot be performed in the wavelet domain; instead the wavelet surface must be transformed into a spectrum (i.e., by performing an inverse wavelet transform to convert the wavelet surface into the time domain and then performing a spectral transform from the time domain). Conversely, operations performed in the wavelet domain cannot be performed in the spectral domain; instead a spectrum must first be transformed into a wavelet surface (i.e., by performing an inverse spectral transform to convert the spectral domain into the time domain and then performing a wavelet transform from the time domain). Nor does a cross-section of the three-dimensional wavelet surface along, for example, a particular point in time equate to a frequency spectrum upon which spectral-based techniques may be used. At least because wavelet space includes a time dimension, spectral techniques and wavelet techniques are not interchangeable. It will be understood that converting a system that relies on spectral domain processing to one that relies on wavelet space processing would require significant and fundamental modifications to the system in order to accommodate the wavelet space processing (e.g., to derive a representative energy value for a signal or part of a signal requires integrating twice, across time and scale, in the wavelet domain while, conversely, one integration across frequency is required to derive a representative energy value from a spectral domain). As a further example, to reconstruct a temporal signal requires integrating twice, across time and scale, in the wavelet domain while, conversely, one integration across frequency is required to derive a temporal signal from a spectral domain. It is well known in the art that, in addition to or as an alternative to amplitude, parameters such as energy density, modulus, phase, among others may all be generated using such transforms and that these parameters have distinctly different contexts and meanings when defined in a two-dimensional frequency coordinate system rather than a three-dimensional wavelet coordinate system. For example, the phase of a Fourier system is calculated with respect to a single origin for all frequencies while the phase for a wavelet system is unfolded into two dimensions with respect to a wavelet's location (often in time) and scale.

The energy density function of the wavelet transform, the scalogram, is defined as $$S(a,b)=|T(a,b)|^2 \quad (10)$$

where '||' is the modulus operator. The scalogram may be rescaled for useful purposes. One common rescaling is defined as $$S_R(a, b) = \frac{|T(a, b)|^2}{a} \qquad (11)$$

and is useful for defining ridges in wavelet space when, for example, the Morlet wavelet is used. Ridges are defined as the locus of points of local maxima in the plane. Any reasonable definition of a ridge may be employed in the method. Also included as a definition of a ridge herein are paths displaced from the locus of the local maxima. A ridge associated with only the locus of points of local maxima in the plane are labeled a "maxima ridge".

For implementations requiring fast numerical computation, the wavelet transform may be expressed as an approximation using Fourier transforms. Pursuant to the convolution theorem, because the wavelet transform is the cross-correlation of the signal with the wavelet function, the wavelet transform may be approximated in terms of an inverse FFT of the product of the Fourier transform of the signal and the Fourier transform of the wavelet for each required a scale and then multiplying the result by $\sqrt{a}$.

In the discussion of the technology which follows herein, the "scalogram" may be taken to include all suitable forms of rescaling including, but not limited to, the original unscaled wavelet representation, linear rescaling, any power of the modulus of the wavelet transform, or any other suitable rescaling. In addition, for purposes of clarity and conciseness, the term "scalogram" shall be taken to mean the wavelet transform, T(a,b) itself, or any part thereof. For example, the real part of the wavelet transform, the imaginary part of the wavelet transform, the phase of the wavelet transform, any other suitable part of the wavelet transform, or any combination thereof is intended to be conveyed by the term "scalogram".

A scale, which may be interpreted as a representative temporal period, may be converted to a characteristic frequency of the wavelet function. The characteristic frequency associated with a wavelet of arbitrary a scale is given by $$f = \frac{f_c}{a} \qquad (12)$$

where $f_c$, the characteristic frequency of the mother wavelet (i.e., at a=1), becomes a scaling constant and f is the representative or characteristic frequency for the wavelet at arbitrary scale a.

Any suitable wavelet function may be used in connection with the present disclosure. One of the most commonly used complex wavelets, the Morlet wavelet, is defined as:

$$\psi(t) = \pi^{-1/4}(e^{i2\pi f_0 t} - e^{-(2\pi f_0)^2/2})e^{-t^2/2} \qquad (13)$$

where $f_0$ is the central frequency of the mother wavelet. The second term in the parenthesis is known as the correction term, as it corrects for the non-zero mean of the complex sinusoid within the Gaussian window. In practice, it becomes negligible for values of $f_0 \gg 0$ and can be ignored, in which case, the Morlet wavelet can be written in a simpler form as $$\psi(t) = \frac{1}{\pi^{1/4}} e^{i2\pi f_0 t} e^{-t^2/2} \qquad (14)$$

This wavelet is a complex wave within a scaled Gaussian envelope. While both definitions of the Morlet wavelet are included herein, the function of equation (14) is not strictly a wavelet as it has a non-zero mean (i.e., the zero frequency term of its corresponding energy spectrum is non-zero). However, it will be recognized by those skilled in the art that equation (14) may be used in practice with $f_0 \gg 0$ with minimal error and is included (as well as other similar near wavelet functions) in the definition of a wavelet herein. A more detailed overview of the underlying wavelet theory, including the definition of a wavelet function, can be found in the general literature. Discussed herein is how wavelet transform features may be extracted from the wavelet decomposition of signals. For example, wavelet decomposition of PPG signals may be used to provide clinically useful information within a medical device.

Figure 3B:
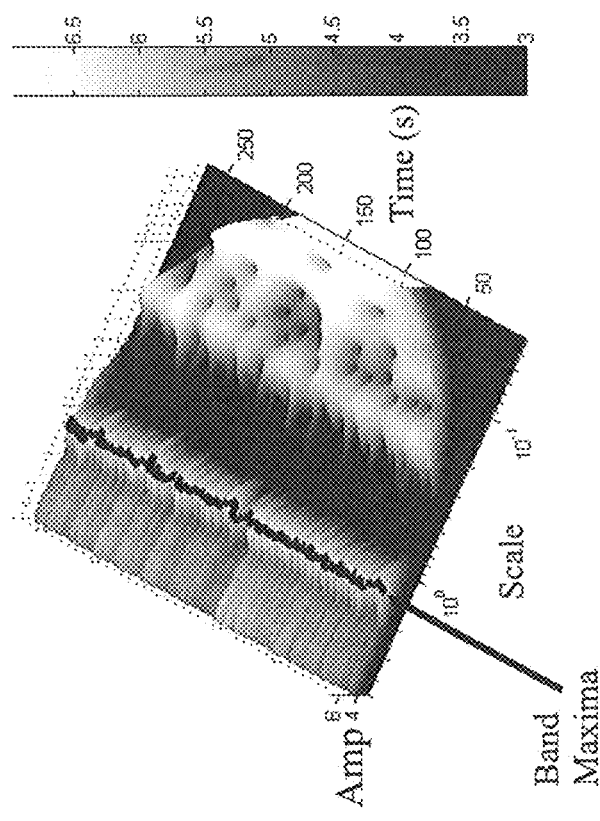
FIGS. 3(a) and 3(b) show illustrative views of a scalogram derived from a PPG signal in accordance with an embodiment.
Figure 3A:
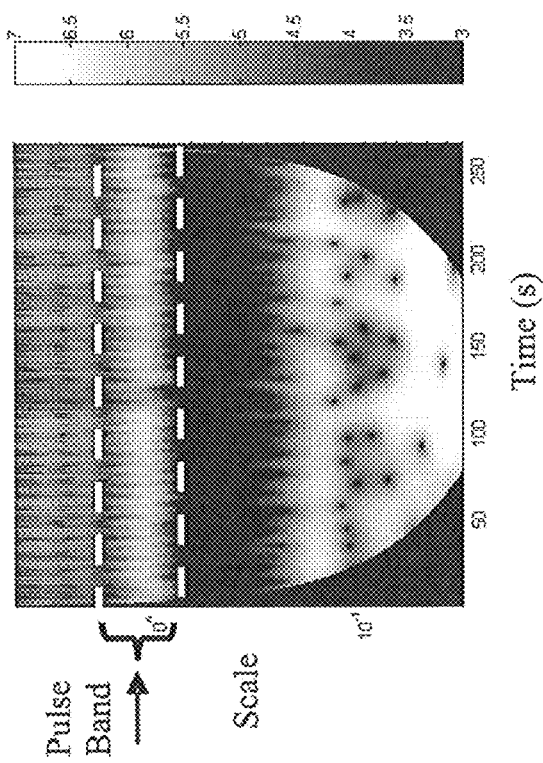

Pertinent repeating features in a signal give rise to a time-scale band in wavelet space or a rescaled wavelet space. For example, the pulse component of a PPG signal produces a dominant band in wavelet space at or around the pulse frequency. FIGS. 3(a) and (b) show two views of an illustrative scalogram derived from a PPG signal, according to an embodiment. The figures show an example of the band caused by the pulse component in such a signal. The pulse band is located between the dashed lines in the plot of FIG. 3(a). The band is formed from a series of dominant coalescing features across the scalogram. This can be clearly seen as a raised band across the transform surface in FIG. 3(b) located within the region of scales indicated by the arrow in the plot (corresponding to 60 beats per minute). The maxima of this band with respect to scale is the ridge. The locus of the ridge is shown as a black curve on top of the band in FIG. 3(b). By employing a suitable rescaling of the scalogram, such as that given in equation (11), the ridges found in wavelet space may be related to the instantaneous frequency of the signal. In this way, the pulse rate may be obtained from the PPG signal. Instead of rescaling the scalogram, a suitable predefined relationship between the scale obtained from the ridge on the wavelet surface and the actual pulse rate may also be used to determine the pulse rate.

By mapping the time-scale coordinates of the pulse ridge onto the wavelet phase information gained through the wavelet transform, individual pulses may be captured. In this way, both times between individual pulses and the timing of components within each pulse may be monitored and used to detect heart beat anomalies, measure arterial system compliance, or perform any other suitable calculations or diagnostics. Alternative definitions of a ridge may be employed. Alternative relationships between the ridge and the pulse frequency of occurrence may be employed.

Figure 3C:
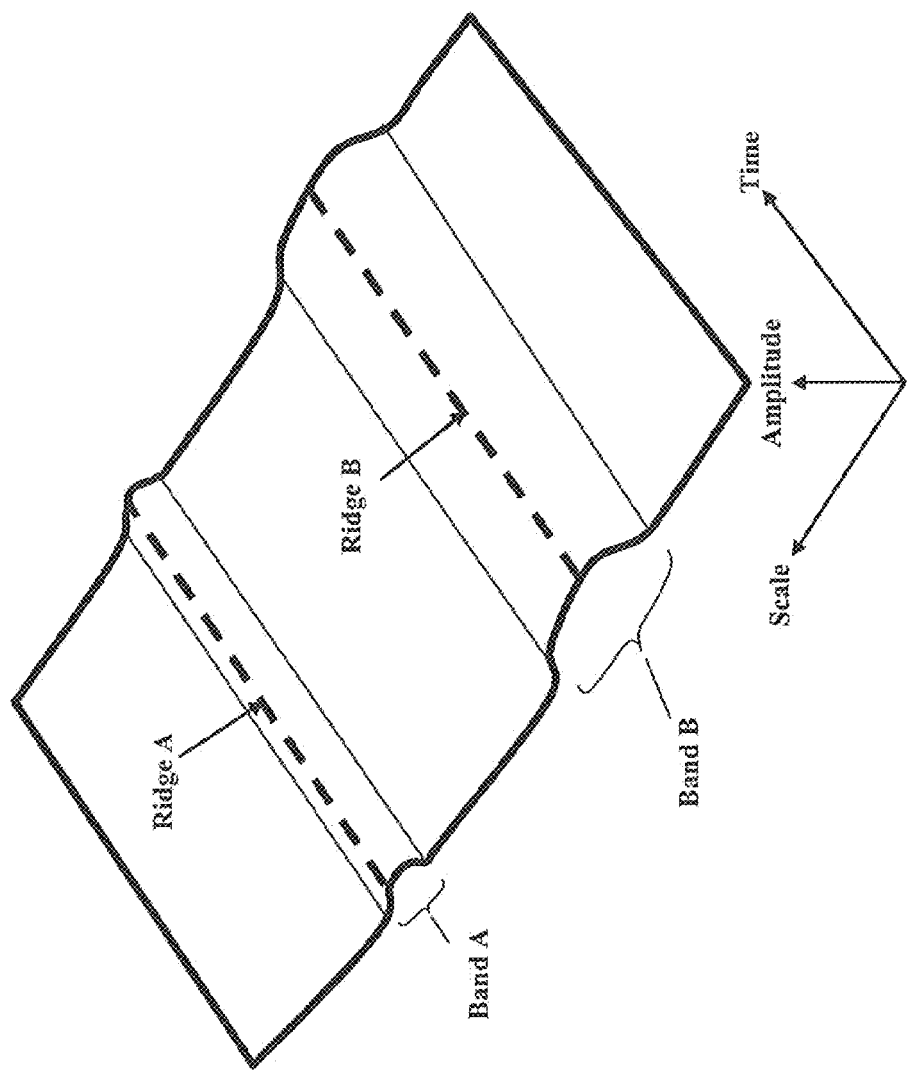
FIG. 3(c) shows an illustrative scalogram derived from a signal containing two pertinent components in accordance with an embodiment.
Figure 3D:
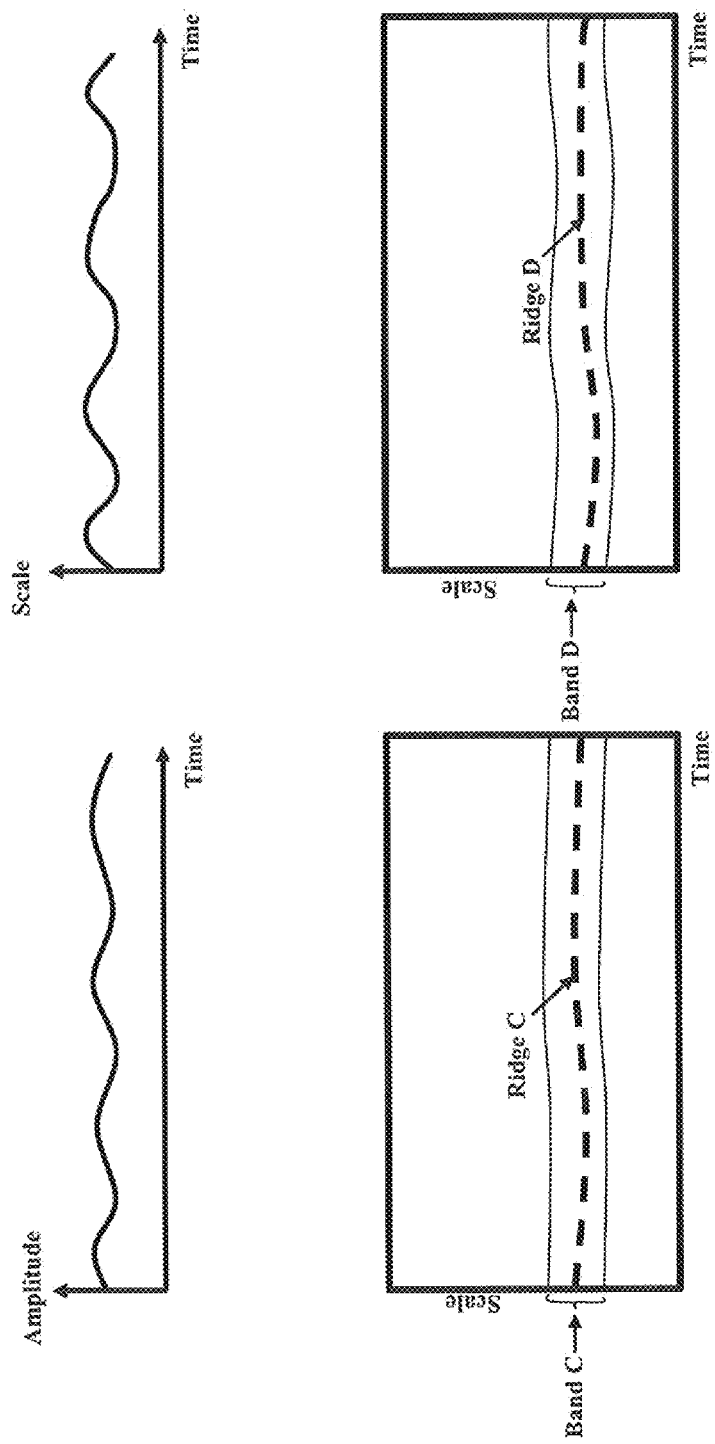
FIG. 3(d) shows an illustrative schematic of signals associated with a ridge in FIG. 3(c) and illustrative schematics of a further wavelet decomposition of these newly derived signals in accordance with an embodiment.

As discussed above, pertinent repeating features in the signal give rise to a time-scale band in wavelet space or a rescaled wavelet space. For a periodic signal, this band remains at a constant scale in the time-scale plane. For many real signals, especially biological signals, the band may be non-stationary; varying in scale, amplitude, or both over time. FIG. 3(c) shows an illustrative schematic of a wavelet transform of a signal containing two pertinent components leading to two bands in the transform space, according to an embodiment. These bands are labeled band A and band B on the three-dimensional schematic of the wavelet surface. In this embodiment, the band ridge is defined as the locus of the peak values of these bands with respect to scale. For purposes of discussion, it may be assumed that band B contains the signal information of interest. This will be referred to as the "primary band". In addition, it may be assumed that the system from which the signal originates, and from which the transform is subsequently derived, exhibits some form of coupling between the signal components in band A and band B. When noise or other erroneous features are present in the signal with similar spectral characteristics of the features of band B then the information within band B can become ambiguous (i.e., obscured, fragmented or missing). In this case, the ridge of band A may be followed in wavelet space and extracted either as an amplitude signal or a scale signal which will be referred to as the "ridge amplitude perturbation" (RAP) signal and the "ridge scale perturbation" (RSP) signal, respectively. The RAP and RSP signals may be extracted by projecting the ridge onto the time-amplitude or time-scale planes, respectively. The top plots of FIG. 3(d) show a schematic of the RAP and RSP signals associated with ridge A in FIG. 3(c). Below these RAP and RSP signals are schematics of a further wavelet decomposition of these newly derived signals. This secondary wavelet decomposition allows for information in the region of band B in FIG. 3(c) to be made available as band C and band D. The ridges of bands C and D may serve as instantaneous time-scale characteristic measures of the signal components causing bands C and D. This technique, which will be referred to herein as secondary wavelet feature decoupling (SWED), may allow information concerning the nature of the signal components associated with the underlying physical process causing the primary band B (FIG. 3(c)) to be extracted when band B itself is obscured in the presence of noise or other erroneous signal features.

In some instances, an inverse continuous wavelet transform may be desired, such as when modifications to a scalogram (or modifications to the coefficients of a transformed signal) have been made in order to, for example, remove artifacts. In one embodiment, there is an inverse continuous wavelet transform which allows the original signal to be recovered from its wavelet transform by integrating over all scales and locations, a and b:

$$x(t) = \frac{1}{C_g} \int_{-\infty}^{\infty} \int_0^{\infty} T(a,b) \frac{1}{\sqrt{a}} \psi\left(\frac{t-b}{a}\right) \frac{da\,db}{a^2} \quad (15)$$

which may also be written as:

$$x(t) = \frac{1}{C_g} \int_{-\infty}^{\infty} \int_0^{\infty} T(a,b) \psi_{a,b}(t) \frac{da\,db}{a^2} \quad (16)$$

where $C_g$ is a scalar value known as the admissibility constant. It is wavelet type dependent and may be calculated from:

$$C_g = \int_0^{\infty} \frac{|\hat{\psi}(f)|^2}{f} df \quad (17)$$

Figure 3E:
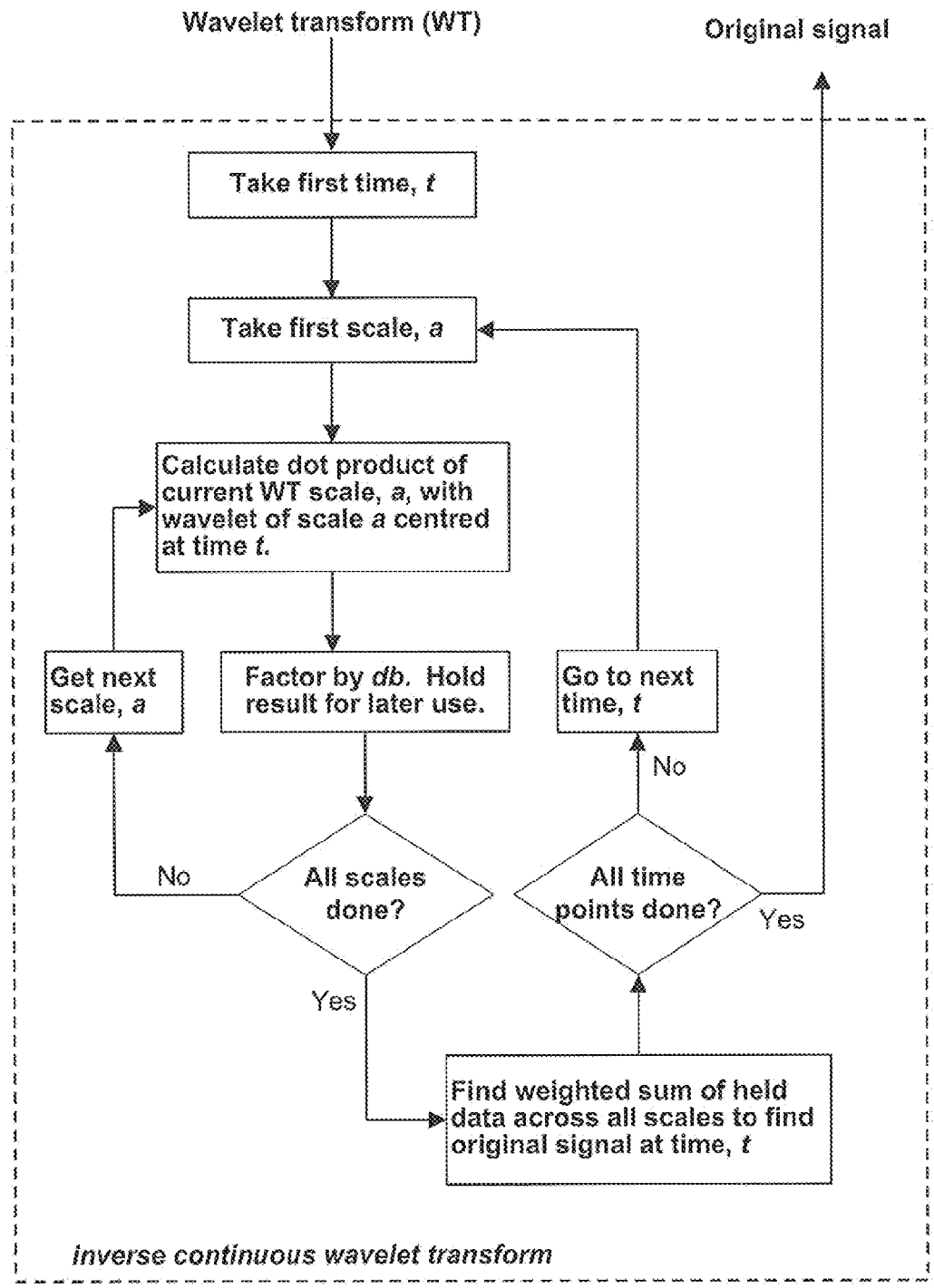
FIGS. 3(e) and 3(f) are flow charts of illustrative steps involved in performing an inverse continuous wavelet transform in accordance with some embodiments.
Figure 3F:
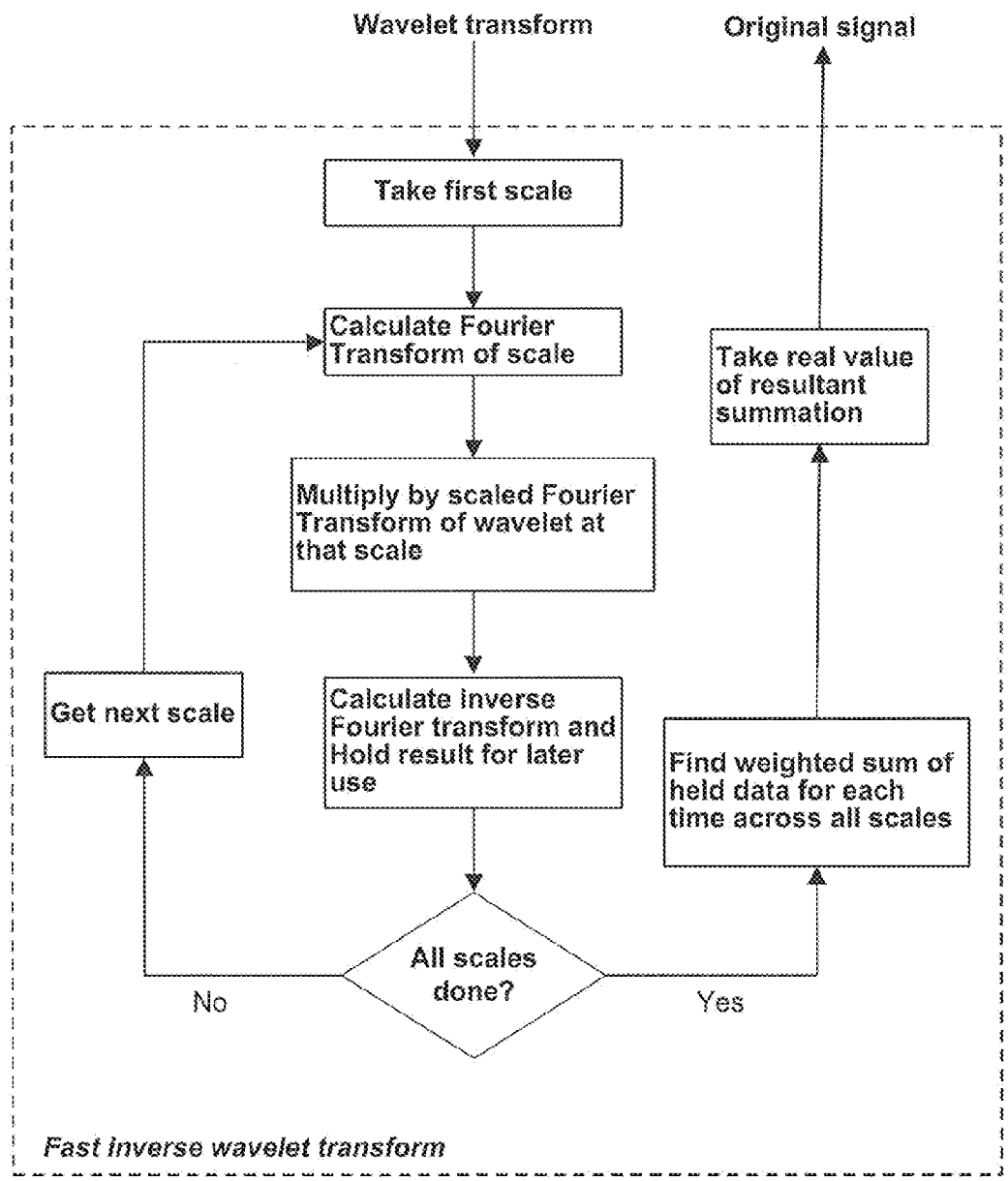

FIG. 3(e) is a flow chart of illustrative steps that may be taken to perform an inverse continuous wavelet transform in accordance with the above discussion. An approximation to the inverse transform may be made by considering equation (15) to be a series of convolutions across scales. It shall be understood that there is no complex conjugate here, unlike for the cross correlations of the forward transform. As well as integrating over all of a and b for each time t, this equation may also take advantage of the convolution theorem which allows the inverse wavelet transform to be executed using a series of multiplications. FIG. 3(f) is a flow chart of illustrative steps that may be taken to perform an approximation of an inverse continuous wavelet transform. It will be understood that any other suitable technique for performing an inverse continuous wavelet transform may be used in accordance with the present disclosure.

Figure 4:
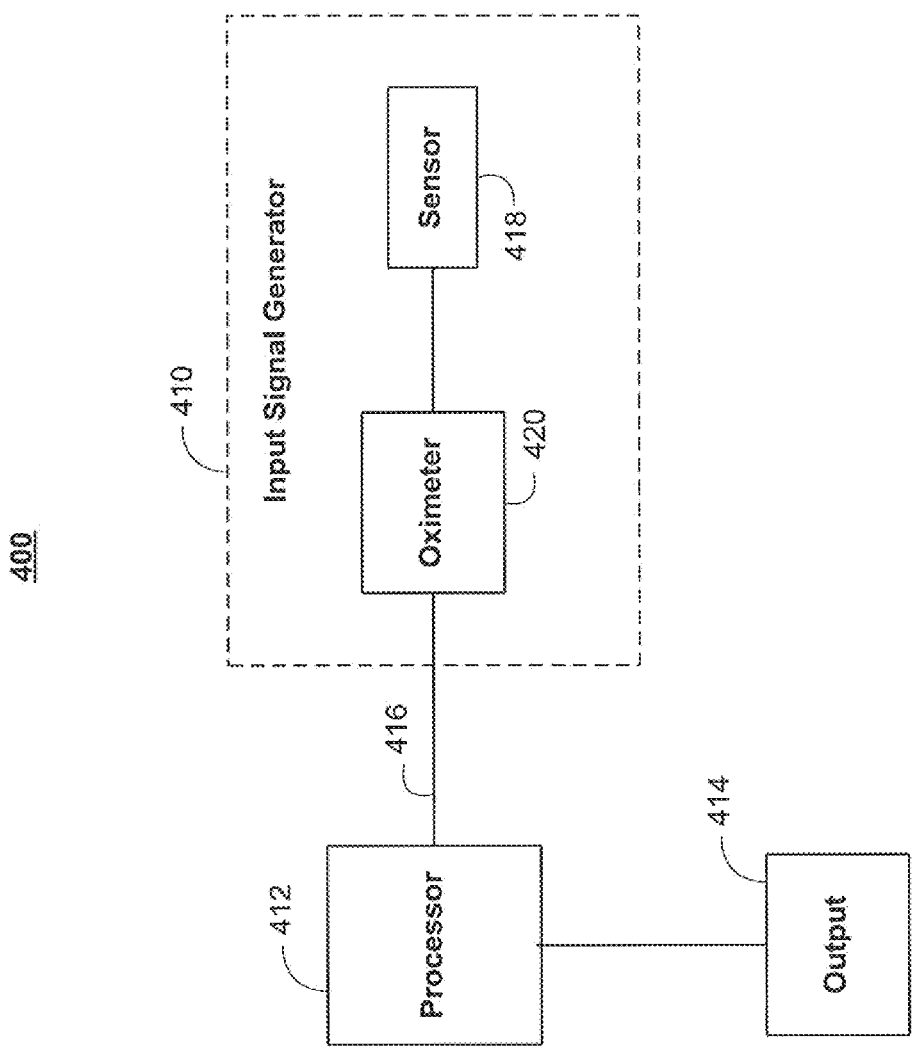
FIG. 4 is a block diagram of an illustrative continuous wavelet processing system in accordance with some embodiments.

FIG. 4 is an illustrative continuous wavelet processing system in accordance with an embodiment. In this embodiment, input signal generator 410 generates an input signal 416. As illustrated, input signal generator 410 may include oximeter 420 coupled to sensor 418, which may provide as input signal 416, a PPG signal. It will be understood that input signal generator 410 may include any suitable signal source, signal generating data, signal generating equipment, or any combination thereof to produce signal 416. Signal 416 may be any suitable signal or signals, such as, for example, biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In this embodiment, signal 416 may be coupled to processor 412. Processor 412 may be any suitable software, firmware, and/or hardware, and/or combinations thereof for processing signal 416. For example, processor 412 may include one or more hardware processors (e.g., integrated circuits), one or more software modules, computer-readable media such as memory, firmware, or any combination thereof. Processor 412 may, for example, be a computer or may be one or more chips (i.e., integrated circuits). Processor 412 may perform the calculations associated with the continuous wavelet transforms of the present disclosure as well as the calculations associated with any suitable interrogations of the transforms. Processor 412 may perform any suitable signal processing of signal 416 to filter signal 416, such as any suitable band-pass filtering, adaptive filtering, closed-loop filtering, and/or any other suitable filtering, and/or any combination thereof.

Processor 412 may be coupled to one or more memory devices (not shown) or incorporate one or more memory devices such as any suitable volatile memory device (e.g., RAM, registers, etc.), non-volatile memory device (e.g., ROM, EPROM, magnetic storage device, optical storage device, flash memory, etc.), or both. The memory may be used by processor 412 to, for example, store data corresponding to a continuous wavelet transform of input signal 416, such as data representing a scalogram. In one embodiment, data representing a scalogram may be stored in RAM or memory internal to processor 412 as any suitable three-dimensional data structure such as a three-dimensional array that represents the scalogram as energy levels in a time-scale plane. Any other suitable data structure may be used to store data representing a scalogram.

Processor 412 may be coupled to output 414. Output 414 may be any suitable output device such as, for example, one or more medical devices (e.g., a medical monitor that displays various physiological parameters, a medical alarm, or any other suitable medical device that either displays physiological parameters or uses the output of processor 412 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

It will be understood that system 400 may be incorporated into system 10 (FIGS. 1 and 2) in which, for example, input signal generator 410 may be implemented as parts of sensor 12 and monitor 14 and processor 412 may be implemented as part of monitor 14.

Figure 5:
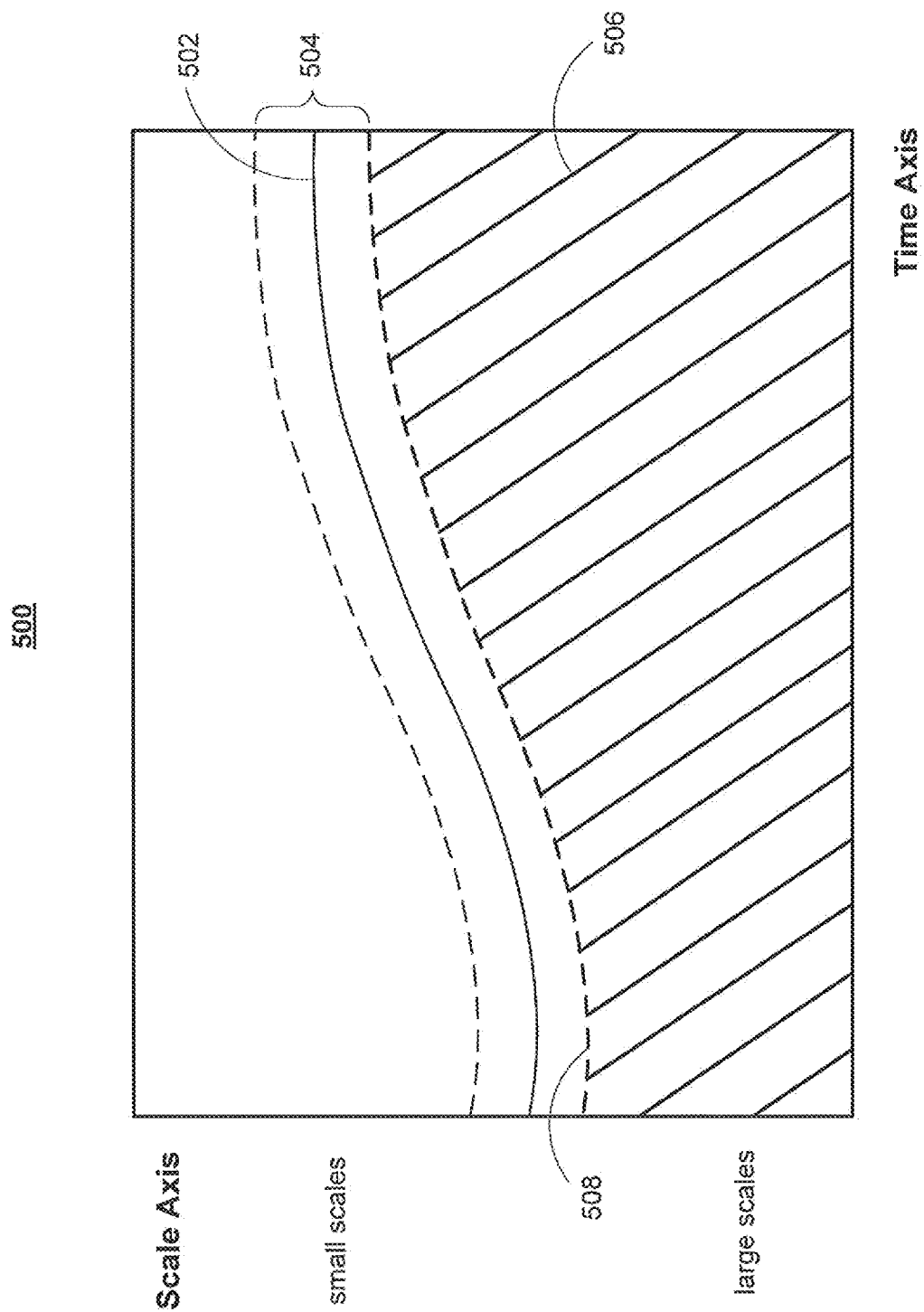
FIG. 5 shows an illustrative diagram of a generalized wavelet scalogram in accordance with an embodiment.

FIG. 5 shows a generalized diagram of wavelet scalogram 500. As described above, one or more ridges may be identified in scalogram 500. For example, a signal processing system may identify pulse band ridge 502 in scalogram 500. The ridge may be defined, in some embodiments, as the maxima with respect to time of the band formed by the pulse components of the signal. As described above, pertinent repeating features in a signal may give rise to a time-scale band in wavelet space or a rescaled wavelet space. For example, the pulse component of a PPG signal may produce a dominant band in wavelet space at or around a scale corresponding to the pulse frequency.

In some embodiments, pulse band ridge 502 may be identified directly from the wavelet transform scalogram. For example, a signal processing system may identify pulse band ridge 502 using any suitable signal processing or signal analysis technique. Pulse band ridge 502 may also be identified using externally supplied data (e.g., a heart rate supplied by a physiological monitoring system or other device), or using both the wavelet transform scalogram and externally supplied data.

After the pulse band ridge is identified, pulse band region 504 may be defined. Pulse band region 504 may be selected to include, for example, the region of influence of the pulse components on the transform surface. In some embodiments, region 504 may extend on one or both sides of pulse band ridge 502 until a threshold roll off of some measure (e.g., energy density) in wavelet scalogram 500 is encountered. In some embodiments, pulse band region 504 may extend on one or both sides of pulse band ridge 502 until some percentage of ridge peak energy is encountered. For example, the pulse band region may extend on one or both sides of the pulse band ridge until a 0.5% ridge peak energy is encountered. Pulse band region 504 may additionally or alternatively be defined as a distance from pulse band ridge 502 on one or both sides of the ridge. In yet another embodiment, pulse band region 504 may be defined using a threshold that sets a minima boundary between the pulse band and another larger-scale band which minimizes the impact of the larger-scale band.

After the pulse band region is defined, lower boundary 508 of this region may be used to partition the pulse information in wavelet scalogram 500 from other larger-scale oscillations in the signal. For example, region 506 of wavelet scalogram 500 at scales larger than pulse band region 504 may contain the larger scale signal components. When an inverse transform (e.g., inverse continuous wavelet transform) is performed on region 506, the original larger-scale (LS) signal may be obtained, but without the DC component (e.g., without the DC offset). The signal baseline, B, may then be computed as the LS signal plus the DC component or DC offset. For example, the DC component may be computed separately, added to the LS signal, and then used to normalize the PPG signal.

In an embodiment, the LS signal may be computed by taking the inverse continuous wavelet transform of the larger-scale components in the wavelet scalogram (e.g., the components at scales larger then the pulse band). The LS signal may then be added to a mean signal component or the DC component to form the baseline B.

More than one baseline signal may be computed in some embodiments. For example, a baseline for a red PPG signal and a baseline for an infrared PPG signal may both be computed (either simultaneously, substantially simultaneously, or serially) and used to normalize the associated PPG signal. Physiological parameters may then be determined from one or more of the normalized PPG signals. For example, oxygen saturation may be determined using the ratio of ratios described above.

Figure 6:
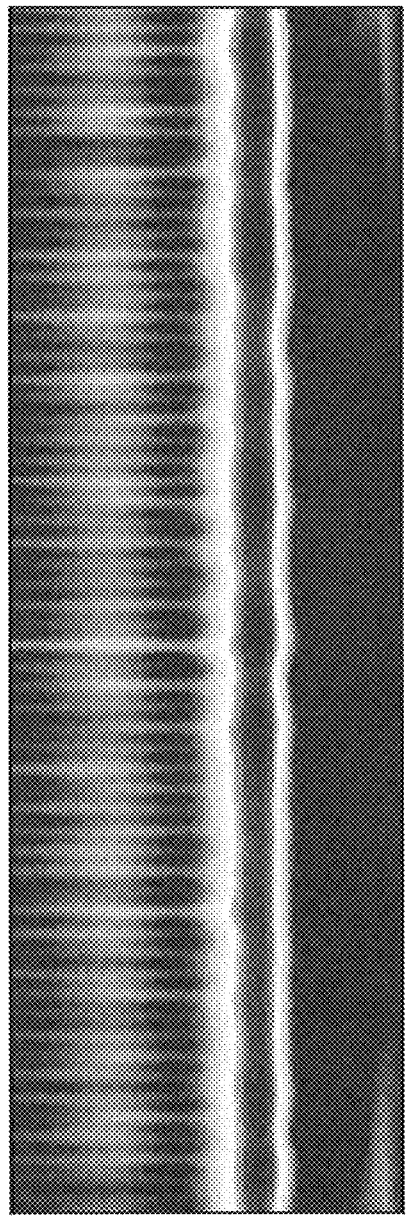
FIG. 6 shows an illustrative wavelet scalogram of a PPG signal in accordance with an embodiment.
Figure 7:
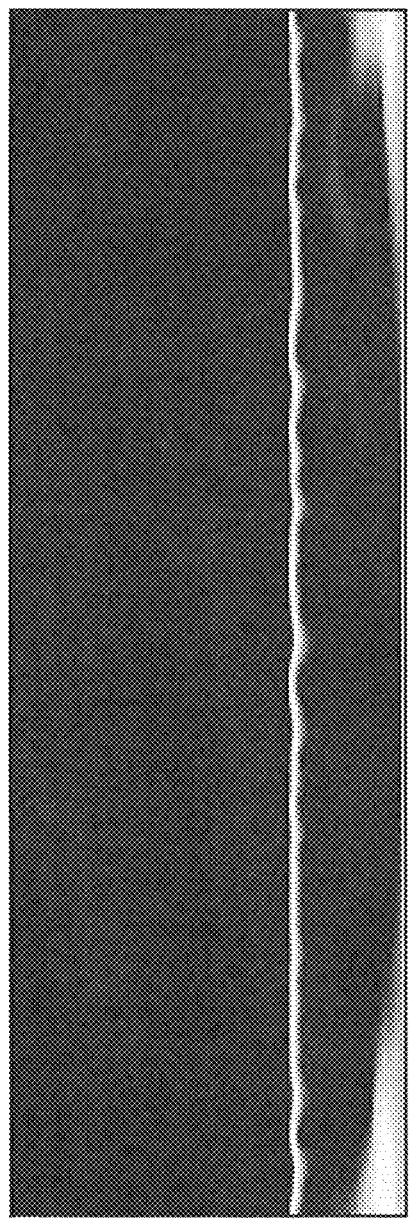
FIG. 7 shows the larger scale components of the illustrative wavelet scalogram of FIG. 6 in accordance with an embodiment.
Figure 8:
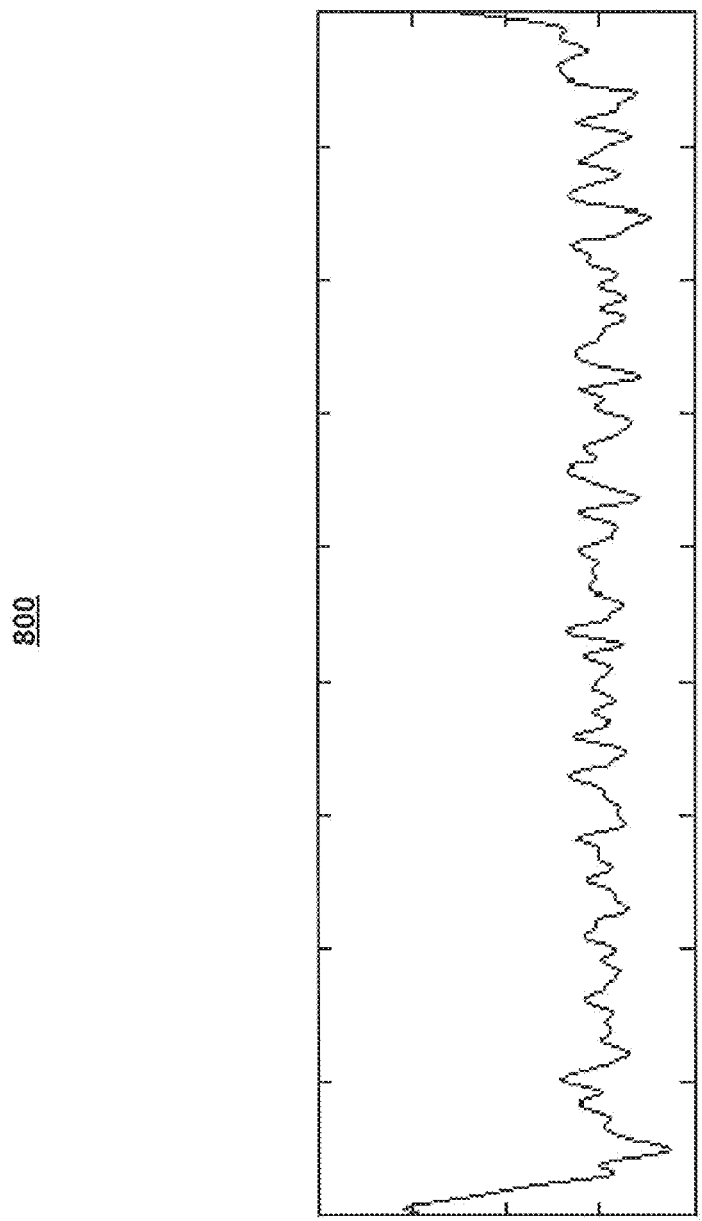
FIG. 8 shows an illustrative baseline signal derived, at least in part, from the larger scale components shown in FIG. 7 in accordance with an embodiment.

FIG. 6 shows illustrative wavelet scalogram 600 of a physiological signal (e.g., a PPG signal). As described above, signal components at scales larger than the pulse band may be identified and used in determining a baseline signal B. In order to isolate the signal components at scales larger than the pulse band, in some embodiments, wavelet transform values corresponding to scales smaller then the pulse band may be set to zero. In other embodiments, these wavelet transform values may actually be removed from the original signal (e.g., PPG signal or transform of the PPG signal) and the original signal reconstructed without these smaller scale components. FIG. 7 shows wavelet scalogram 700, which is the scalogram of FIG. 6 with wavelet transform values corresponding to scales smaller then the pulse band set to zero (or removed). After setting the smaller order scales to zero, an inverse wavelet transform of this "cropped" scalogram may then be added to the DC component of the signal to produce a baseline signal B. FIG. 8 shows illustrative baseline signal 800 derived, at least in part, from wavelet scalogram 700. This baseline signal may then be used to normalize the physiological signal (e.g., the PPG signal, any transform thereof, or any wavelet scalogram of any transform thereof). Oxygen saturation (and other physiological parameters) may then be determined from the normalized signal using any suitable method. For example, as described above, a ratio of ratios may be taken from red and infrared PPG signals and used to determine oxygen saturation using, for example, equations (4) and (5) above.

The baseline signal B may be derived directly from the received physiological signal itself (e.g., a PPG signal), some transform of the received physiological signal (e.g., a continuous wavelet transform), a scalogram derived from the transformed signal, a wavelet ratio surface, the real part of the wavelet transform, the imaginary part of the wavelet transform, the modulus of the wavelet transform, the energy density of the wavelet transform, or any combination of the foregoing signals. For example, in some embodiments, an inverse wavelet transform may not be performed in order to obtain the baseline signal B. For example, a measure proportional to the local amplitude of the entire PPG signal and a measure proportional to the amplitude of the baseline may be extracted from the wavelet transform (e.g., wavelet transform 600 of FIG. 6) without performing the inverse wavelet transform. This may be accomplished, for example, by expressing the energy of the DC component in units proportional to the wavelet transform modulus values. Any other suitable technique for determining the baseline signal B in the wavelet domain may be used in other embodiments.

Figure 9:
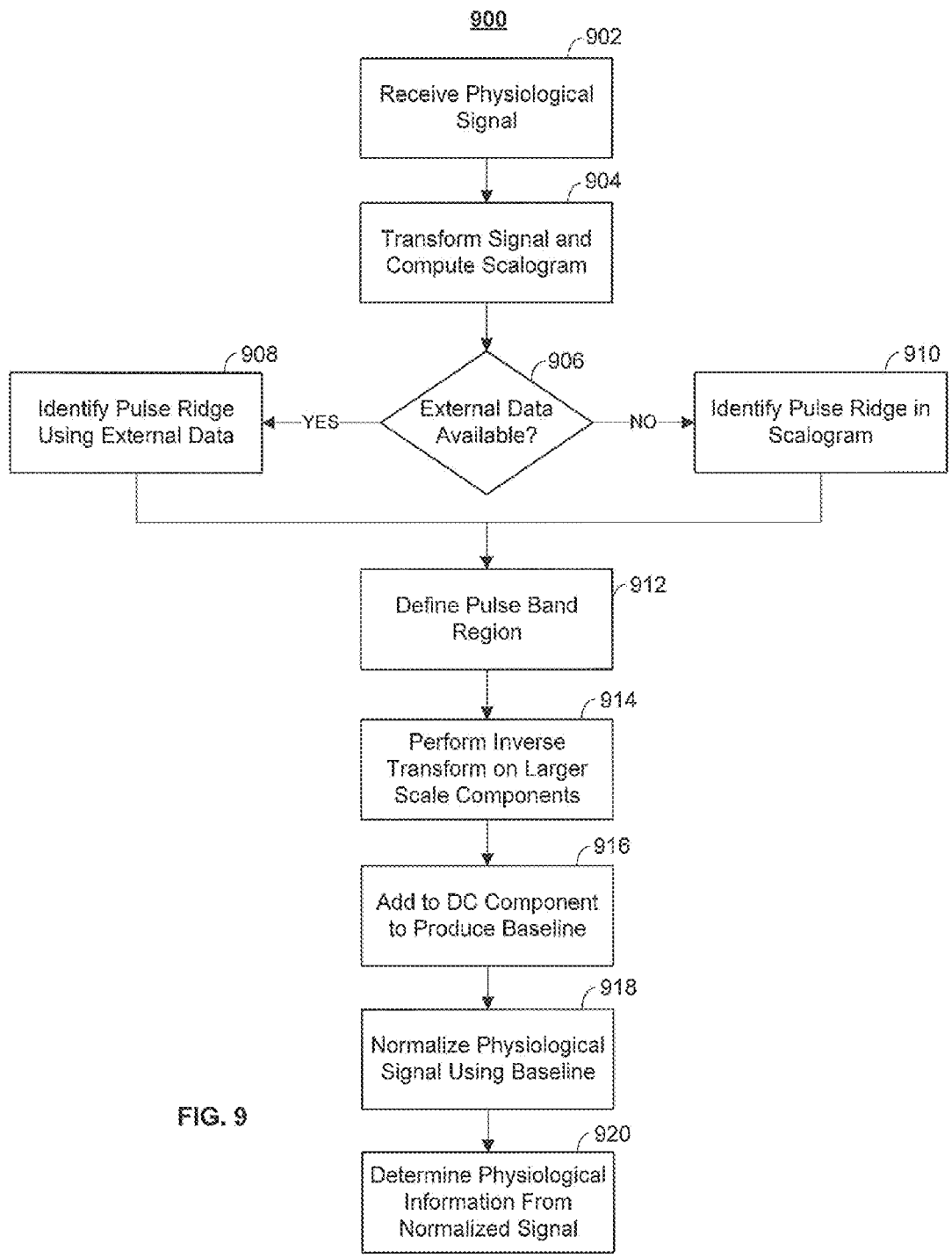
FIG. 9 shows an illustrative processes for determining at least one physiological parameter in accordance with some embodiments.

FIG. 9 shows illustrative process 900 for determining at least one physiological parameter using a baseline signal computed at least partially in the wavelet domain. At step 902, a physiological signal may be received. For example, one or more PPG signals may be received from sensor 12 (FIG. 2) at step 902. One of the received signals may include, for example, a red PPG signal while another received signal may include, for example, an infrared PPG signal. At step 904, the received signal or signals may be transformed using, for example, a continuous wavelet transform, and a wavelet scalogram may be computed. At step 906, a determination is made whether external data is available to help identify a pulse ridge in the wavelet scalogram. Various types of external data may be helpful in determining the pulse band ridge location. For example, external data in the form of a patient's heart rate may be supplied by monitor 14 (FIG. 2) or some other physiological monitoring system and used to identify the pulse band ridge in a wavelet scalogram (e.g., wavelet scalogram 600 of FIG. 6). If external data is available at step 906, the pulse band ridge is identified at step 908 using, at least in part, the available external data. If no external data is available at step 906, then the pulse band ridge may be identified directly from the wavelet scalogram at step 910. For example, any suitable signal processing or signal analysis technique may be used to determine the pulse band ridge. In other embodiments, both external data and the wavelet scalogram itself may be used to identify the pulse band ridge.

After the pulse band ridge is identified, at step 912 the pulse band region may be defined. For example, the pulse band region may be defined to include, for example, the region of influence of the pulse components on the transform surface. In some embodiments, the pulse band region may extend on one or both sides of the pulse band ridge until a threshold roll off of some measure (e.g., energy density) in the wavelet scalogram is encountered. In some embodiments, the pulse band region may extend on one or both sides of the pulse band ridge until some percentage of ridge peak energy is encountered. For example, the pulse band region may extend on one or both sides of the pulse band ridge until a 0.5% ridge peak energy is encountered. The pulse band region may additionally or alternatively be defined as a distance from the pulse band ridge on one or both sides of the ridge in the wavelet scalogram. In yet another embodiment, the pulse band region may be defined using a threshold that sets a minima boundary between the pulse band and another larger-scale band which minimizes the impact of the larger-scale band.

At step 914, an inverse transform (e.g., an inverse continuous wavelet transform) may be performed on the components of the wavelet scalogram that are at larger scales than the pulse band region defined at step 912. For example region 506 (FIG. 5) of wavelet scalogram 500 (FIG. 5), which appears below pulse band region 504 (FIG. 5) in wavelet scalogram 500 (FIG. 5), may be at scales larger than pulse band region 504 (FIG. 5). Additionally or alternatively, at step 914, the inverse transform may be performed on regions of the scalogram that are at different characteristic frequencies than the pulse band region. For example, regions above, below, or both above and below the defined pulse band region may be used in some embodiments. After the inverse wavelet transform is performed, the original physiological signal may be obtained, but without the DC offset component of the signal. At step 916, the DC component may be added to the result of the inverse transform to form the baseline signal B. At step 918, the physiological signal received at step 902 (or some transform of that signal) may be normalized using the baseline signal B. For example, the signal received at step 902 (or some transform of that signal) may be divided by the baseline signal to produce a normalized signal.

At step 920, physiological information (e.g., at least one physiological parameter) may be determined from the normalized signal. For example, as described above, a ratio of ratios may be computed using, for example, red and infrared PPG signals in order to determine oxygen saturation. Other physiological information (e.g., heart rate, respiration rate, respiratory effort, and blood pressure) may also be determined using the normalized signal at step 920.

The foregoing is merely illustrative of the principles of this disclosure and various modifications can be made by those skilled in the art without departing from the scope and spirit of the disclosure. The above described embodiments are presented for purposes of illustration and not of limitation. The present disclosure also can take many forms other than those explicitly described herein. Accordingly, it is emphasized that the disclosure is not limited to the explicitly disclosed methods, systems, and apparatuses, but is intended to include variations to and modifications thereof which are within the spirit of the following claims.

What is claimed is:

1. A method for processing a plethysmograph signal comprising:
using processing circuitry for:
receiving, from a sensor, the plethysmograph signal,
transforming the received plethysmograph signal using a continuous wavelet transform,
computing a scalogram of the plethysmograph signal based at least in part on the transformed signal,
defining a pulse band region in the scalogram,
identifying at least some components of the scalogram below the pulse band region,
computing the inverse continuous wavelet transform of the identified components,
generating a baseline signal based at least in part on the computed inverse continuous wavelet transform of the identified components and a DC component of the received plethysmograph signal, and
determining physiological information based at least in part on the baseline signal; and
outputting the physiological information to an output device.

2. The method of claim 1 further comprising using the processing circuitry for normalizing the received plethysmograph signal using the baseline signal.

3. The method of claim 2 wherein normalizing the received plethysmograph signal comprises dividing the received plethysmograph signal by the baseline signal.

4. The method of claim 1 wherein determining physiological information comprises determining oxygen saturation, respiration rate, and/or respiration effort.

5. The method of claim 1 wherein defining a pulse band region in the scalogram comprises:
identifying a pulse band ridge in the scalogram; and
determining a roll off in energy density on one or more sides of the defined pulsed band ridge.

6. The method of claim 1 wherein defining a pulse band region in the scalogram comprises receiving external data relating to the pulse band region, wherein the pulse band region is defined, at least in part, using the received external data.

7. The method of claim 6 wherein receiving external data comprises receiving heart rate data from an external physiological monitoring system.

8. The method of claim 1 wherein generating a baseline signal comprises adding the DC component to the inverse continuous wavelet transform of the identified components.

9. The method of claim 1 wherein receiving, from a sensor, the plethysmograph signal comprises receiving, from the sensor, a red photoplethysmograph signal and an infrared photoplethysmograph signal.

10. The method of claim 9 wherein determining physiological information comprises determining oxygen saturation based at least in part on the received red photoplethysmograph signal and the received infrared photoplethysmograph signal.

11. A system for processing a plethysmograph signal, comprising:
a sensor configured to receive the plethysmograph signal;
processing circuitry configured to:
transform the received plethysmograph signal using a continuous wavelet transform,
compute a scalogram of the plethysmograph signal based at least in part on the transformed signal,
define a pulse band region in the scalogram,
identify at least some components of the scalogram below the pulse band region,
compute the inverse continuous wavelet transform of the identified components,
generate a baseline signal based at least in part on the computed inverse continuous wavelet transform of the identified components and a DC component of the received plethysmograph signal, and
determine physiological information based at least in part on the baseline signal; and
an output device to receive the physiological information.

12. The system of claim 11 wherein the processing circuitry is configured to normalize the received plethysmograph signal using the baseline signal.

13. The system of claim 12 wherein the processing circuitry is configured to normalize the received plethysmograph signal by dividing the received plethysmograph signal by the baseline signal.

14. The system of claim 11 wherein the processing circuitry is configured to determine oxygen saturation, respiration rate, and/or respiration effort.

15. The system of claim 11 wherein the processing circuitry is configured to define a pulse band region in the scalogram by:
identifying a pulse band ridge in the scalogram; and
determining a roll off in energy density on one or more sides of the defined pulsed band ridge.

16. The system of claim 11 wherein the processing circuitry is configured to define a pulse band region in the scalogram by receiving external data relating to the pulse band region, wherein the pulse band region is defined, at least in part, using the received external data.

17. The system of claim 16 wherein the processing circuitry is configured to receive heart rate data from an external physiological monitoring system.

18. The system of claim 11 wherein the processing circuitry is configured to generate a baseline signal by adding the DC component to the inverse continuous wavelet transform of the identified components.

19. The system of claim 11 wherein the sensor is configured to receive a red photoplethysmograph signal and an infrared photoplethysmograph signal.

20. The system of claim 19 wherein the processing circuitry is configured to determine oxygen saturation based at least in part on the received red photoplethysmograph signal and the received infrared photoplethysmograph signal.

* * * * *